US008888756B2

(12) United States Patent
Ishiwata et al.

(10) Patent No.: US 8,888,756 B2
(45) Date of Patent: Nov. 18, 2014

(54) PLUG FOR CONTAINER

(75) Inventors: Shunji Ishiwata, Higashiosaka (JP); Atsushi Taga, Higashiosaka (JP); Hideki Fujita, Higashiosaka (JP); Shozo Nishida, Higashiosaka (JP); Ayako Kita, Higashiosaka (JP); Reiko Sugiura, Higashiosaka (JP)

(73) Assignee: GTO Ltd., Osaka (JP)

( * ) Notice: Subject to any disclaimer, the term of this patent is extended or adjusted under 35 U.S.C. 154(b) by 109 days.

(21) Appl. No.: 13/138,803

(22) PCT Filed: Mar. 26, 2010

(86) PCT No.: PCT/JP2010/055466
§ 371 (c)(1),
(2), (4) Date: Nov. 1, 2011

(87) PCT Pub. No.: WO2010/113823
PCT Pub. Date: Oct. 7, 2010

(65) Prior Publication Data
US 2013/0085466 A1 Apr. 4, 2013

(30) Foreign Application Priority Data
Mar. 30, 2009 (JP) ................................ P2009-083682

(51) Int. Cl.
*A61B 19/00* (2006.01)
*B65D 51/00* (2006.01)
*A61J 1/14* (2006.01)

(52) U.S. Cl.
CPC ............. *A61J 1/1412* (2013.01); *B65D 51/002* (2013.01); *A61J 1/1406* (2013.01); *A61J 1/1475* (2013.01)
USPC ........................................... 604/415; 604/411

(58) Field of Classification Search
CPC ...................................................... A61J 1/1406
USPC ........................... 604/411, 406, 415; 215/247
See application file for complete search history.

(56) References Cited

U.S. PATENT DOCUMENTS 2,186,888 A * 1/1940 Tullar et al. .................... 215/248
3,017,050 A * 1/1962 Barr, Sr. et al. ............... 215/247
(Continued)

FOREIGN PATENT DOCUMENTS

JP U 47-13346 10/1972
JP 61-228865 A 10/1986
(Continued)

OTHER PUBLICATIONS

PCT International Preliminary Report on Patentability dated Nov. 24, 2011 for Application No. PCT/JP2010/055466 and English translation thereof.

(Continued)

*Primary Examiner* — Leslie Deak
(74) *Attorney, Agent, or Firm* — Harness, Dickey & Pierce, PLC

(57) ABSTRACT

A plug for a container capable of improving air-tightness and liquid-tightness is provided. A plug includes a first split piece having a cylindrical first fitting portion to be mounted on an opening portion of a container body and fitted to an opening portion space of the opening portion, an end wall which blocks one end of the first fitting portion, and a first flange portion extending outwardly in a radial direction of the first fitting portion from the other end thereof; and a second split piece having a second fitting portion which is fitted to the first fitting portion of the first split piece and forms a closed space between the end wall and the second fitting portion and a second flange portion extending outwardly in a radial direction of the second fitting portion therefrom.

6 Claims, 8 Drawing Sheets

(56) References Cited

U.S. PATENT DOCUMENTS

| | | | | | |
|---|---|---|---|---|---|
| 4,152,269 | A | * | 5/1979 | Babson | 210/516 |
| 4,187,893 | A | * | 2/1980 | Bujan | 604/408 |
| 4,226,333 | A | * | 10/1980 | Percarpio | 215/247 |
| 4,243,150 | A | * | 1/1981 | Gunne et al. | 215/247 |
| 4,582,207 | A | | 4/1986 | Howard et al. | |
| 4,682,703 | A | | 7/1987 | Kasai et al. | |

FOREIGN PATENT DOCUMENTS

| | | |
|---|---|---|
| JP | 61-247459 A | 11/1986 |
| JP | U 62-160941 | 10/1987 |
| JP | 6-335514 A | 12/1994 |
| JP | 2001-289743 A | 10/2001 |
| JP | 2002345925 A | 12/2002 |
| JP | 2004-269038 A | 9/2004 |

OTHER PUBLICATIONS

Japanese Office Action dated Apr. 2, 2013 for corresponding Japanese Application No. 2011-507164 (full translation provided).

Japanese Decision of Refusal for corresponding Japanese Application No. 2011-507164 (full translation provided).

European Office Action dated Aug. 28, 2013.

* cited by examiner

FIG. 9 (CONVENTIONAL)
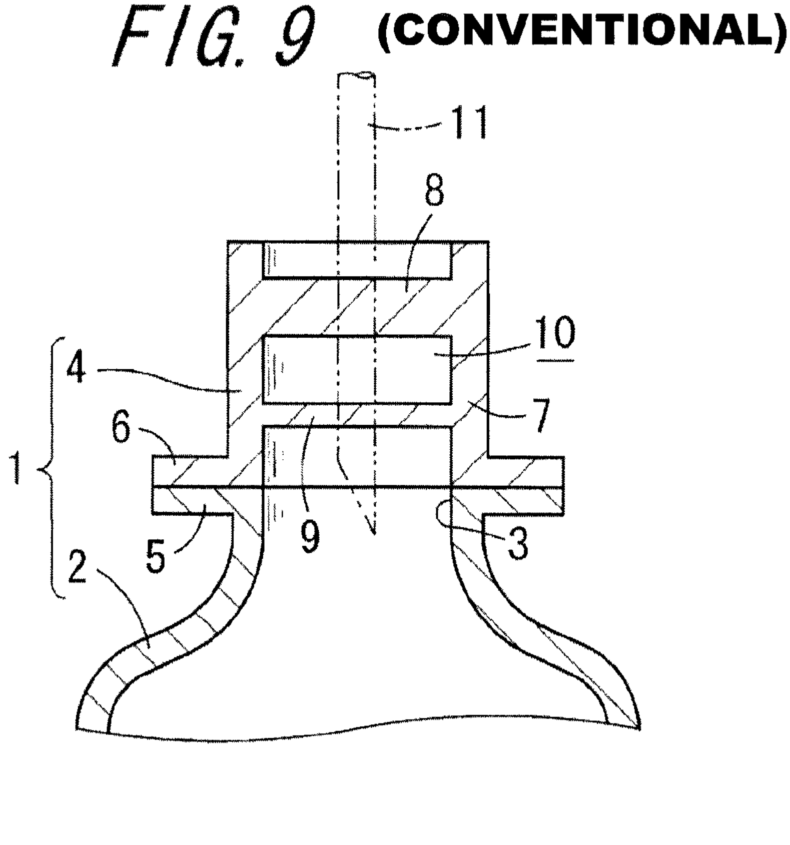

PLUG FOR CONTAINER

TECHNICAL FIELD

The present invention relates to a plug used for a container for containing liquid such as a drug solution.

BACKGROUND ART

For example, since an anti-cancer drug used for treating cancer is used by being prepared in an infusion solution, there is a risk that a healthcare professional who handles the anti-cancer drug would be exposed thereto in administering the anti-cancer drug and discarding thereafter a container which contained the anti-cancer drug. Many anti-cancer drugs have cytotoxicity since these drugs inhibit cell division not only of cancer cells but of normal cells, and are known to have mutagenicity, teratogenicity, and carcinogenicity. Particularly, regarding carcinogenicity, it has been confirmed that anti-cancer drugs such as cyclophosphamide, azathioprine, and the like have a carcinogenic action with respect to the human body.

The risk to the healthcare professional who handles the anti-cancer drug is determined not only by the strength of the toxicity of the drug, but by the body intake amount and the intake period due to the aspiration of the aerosolized drug through the respiratory tract during handling, the attachment of droplets of a drug solution to the skin, the oral intake or the like. Accordingly, since a healthcare professional who handles the anti-cancer drug for a long time is likely to take in the drug for a long time even if the amount is very small, there is a demand for improving the sealing function realized by a plug of a container such as a vial that contains a drug solution of an anti-cancer drug.

Regarding these problems, a technique is used. In the technique, a preparation operation such as mixing of drug solutions is performed in a cabinet in which a closed operation space can be specified, whereby the drug solution is prevented from diffusing outside the cabinet, and the risk that the healthcare professional may be exposed to the drug is reduced. However, even when the operation is performed in the cabinet, the scattering range of the drug solution is unexpectedly wide and a medium to which the drug solution has been attached may be carried out of the cabinet, thereby contaminating the surrounding environment. Consequently, it has been proved that a healthcare professional cannot avoid exposure to the drug even if a cabinet is used.

Therefore, systems are being developed in which a dedicated device is directly connected to the container that contains the anti-cancer drug. However, many of the systems have so far failed to solve the problem that the amount of the leaked drug solution is large. Some of the systems include a device that has a small amount of the leaked drug solution and is excellent in functionality. However, this device is very expensive and requires a complicated operation, so there is a problem in that the practicality is low. Although a container that has a small amount of the leaked drug solution is also being developed, there is a limitation on the types of containers that can be connected thereto, so there is a problem in that there is a lack of versatility.

As another related art for solving problems of the respective related arts that relate to the cabinet, the dedicated connection device, and the container that has a small amount of leaked drug solution, a plug for a container is disclosed as a stopper for an injection in Patent Literature 1, for example.

FIG. 9 is a cross-sectional view showing a plug 4 of a container according to another related art. In the related art disclosed in Patent Literature 1, a container 1 includes a container body 2 that contains a drug solution and a plug 4 that seals an opening portion 3 of the container body 2.

The plug 4 includes a flange portion 6 that is placed on a flange 5 at the body side formed in the opening portion 3 of the container body 2, a cylindrical peripheral wall 7 having one end connected to an inner peripheral portion of the flange portion 6 at a right angle, an end wall 8 that is integrally formed in the other end of the peripheral wall 7, and a partition wall 9 that is integrally formed inside a radial direction of the peripheral wall 7 from a middle portion thereof. In the peripheral wall 7, a closed space 10 is formed between the end wall 8 and the partition wall 9.

CITATION LIST

Patent Literature

Patent Literature 1: Japanese Unexamined Patent Publication JP-A 6-335514 (1994)

SUMMARY OF INVENTION

Technical Problem

In the related art, the plug 4 has a problem in that when inserted injection needle 11 is pulled out, at the time when the tip of the injection needle 11 is taken out from the inner space of the container body 2, passes through the partition wall 9, and is pulled toward the closed wall 10 side, the drug solution that leaks inside the closed space 10 from a crack that is formed when the injection needle 11 is inserted into the partition wall 9 cannot be reliably prevented from leaking outside from a crack formed in the end wall 8.

An object of the invention is to provide a plug for a container that has a simple configuration, is inexpensive, and can reliably prevent the leakage of liquid when an inserted needle is pulled.

Solution to Problem

The invention provides a plug for a container including a first split piece formed of a flexible and resilient material, the first split piece having a cylindrical fitting portion to be mounted on and fitted to an opening portion of a container body containing liquid, the cylindrical fitting portion provided with an opening formed on one end side thereof and an opening formed on the other end side thereof, an end wall which blocks the opening formed on the one end side, and a first flange portion extending outwardly in a radial direction of the fitting portion from the other end thereof; and a second split piece formed of a flexible and resilient material, the second split piece having a partition wall which blocks the opening formed on the other end side and forms a closed space between the end wall and the partition wall and a second flange portion extending outwardly in a radial direction of the partition wall therefrom and being disposed so as to be placed on the first flange portion.

In addition, in the invention, it is preferable that an absorber formed of a liquid-absorbing material is contained in the closed space.

Furthermore, in the invention, it is preferable that In the closed space, the end wall of the first split piece and the partition wall of the second split piece are separated from each other at an interval which is equal to or longer than a length in an axial direction of an end surface of a tip portion of an injection needle that is inserted through the partition wall.

Furthermore, in the invention, it is preferable that the liquid is a drug solution.

Furthermore, in the invention, it is preferable that a water-absorptive polymer is contained in the closed space.

Advantageous Effects of Invention

According to the invention, a plug mounted on an opening portion of a container body is configured with a first split piece and a second split piece. The first and second split pieces are formed of a flexible and resilient material. While the split pieces are mounted on the opening portion of the container body, the fitting portion of the first split piece is fitted into the opening portion of the container body, the second flange portion is placed on the first flange portion, and the closed space is formed between the end wall and the partition wall. Accordingly, it is possible to separately sterilize the whole surface by separately producing the first and second split pieces and to form a clean closed space.

While the first and second split pieces are combined and mounted on the opening portion of the container body, the outer peripheral surface of the fitting portion comes into contact with the inner peripheral surface of the opening portion of the container body, the first flange portion comes into contact with the end surface of the opening portion of the container body, and the second flange portion of the second split piece is placed on the first flange portion. Since the first and second split pieces are formed of a flexible and resilient material, the first flange portion tightly adheres to the end surface of the opening portion of the container body, and the second flange portion tightly adheres to the first flange portion, whereby high air-tightness and liquid-tightness can be accomplished.

In addition, the first and second flange portions are provided while being placed on the opening portion of the container body. Consequently, the end wall formed while being connected to an in-plane direction of the first flange portion and the partition wall formed while being connected to an in-plane direction of the second flange portion more easily undergo elastic deformation compared to the first and second flange portions. As a result, when an inserted injection needle is taken out from the end wall and the partition wall, the end wall and the partition wall undergo the elastic deformation toward the outside by a sliding friction force between the injection needle and the end wall and a sliding friction force between the injection needle and the partition wall.

Therefore, when the injection needle is taken out from the end wall, even when the liquid in the container body leaks inside the closed space from a gap between a crack of the end wall that is formed due to the insertion of the injection needle and the injection needle, the partition wall undergoes the elastic deformation to the outside due to the sliding friction force caused by pulling of the injection needle. Therefore, a negative pressure is created in the closed space, and the negative pressure acts in the gap between the crack of the partition wall and the injection needle. As a result, when the injection needle is taken out from the partition wall, it is possible to reliably prevent the liquid from leaking outside from the gap between the crack of the partition wall and the injection needle. In addition, since the first and second split pieces can be easily realized by a well-known molding technique such as compression molding that uses a metal mold, it is possible to produce a leakage-free plug at a low cost.

In addition, according to the invention, since an absorber formed of a liquid-absorbing material is contained in the closed space, the liquid that leaks inside the closed space is absorbed into the absorber. Therefore, it is possible to more reliably prevent the liquid from leaking between the crack of the partition wall and the injection needle.

Furthermore, according to the invention, since the closed space includes a region having an interval equal to or larger than the length in the axial direction of the end surface of the tip portion of the injection needle, a period is not created in which the tip portion of the injection needle is partially present in both the end wall and the partition wall at the same time. Consequently, when the injection needle is taken out from the end wall and the partition wall, at the time when the wedge-like tip portion of the injection needle passes through the end wall, a right cylinder-like portion that is closer to the base portion than to the tip portion of the injection needle passes through the partition wall, and the partition wall uniformly comes into contact with almost the entire outer peripheral surface of the injection needle. Accordingly, a state is prevented in which the crack formed in the end wall and the crack formed in the partition wall are not incompletely closed at the same time, and it is possible to more reliably prevent the leakage of liquid.

Furthermore, according to the invention, the leakage of liquid can be suppressed with a high sealing performance by the plug. Therefore, when the liquid is a drug solution such as an anti-cancer drug, the handler is prevented from being exposed to the drug solution, and it is possible to significantly improve the safety with respect to the exposure to the drug solution at a low cost.

Furthermore, according to the invention, a water-absorptive polymer is contained in the closed space. Accordingly, when the injection needle is taken out from the end wall, the liquid that leaks inside the closed space can be polymerized by the water-absorptive polymer and captured in the closed space as sol-like or gel-like fluid. Consequently, it is possible to more reliably prevent the leakage of liquid.

BRIEF DESCRIPTION OF DRAWINGS

FIG. 7 is seen from below;

FIG. 9 is a cross-sectional view showing a plug 4 of a container according to another related art;

DESCRIPTION OF EMBODIMENTS

Now, preferred embodiments of the invention will be described in detail with reference to drawings.

Figure 1:
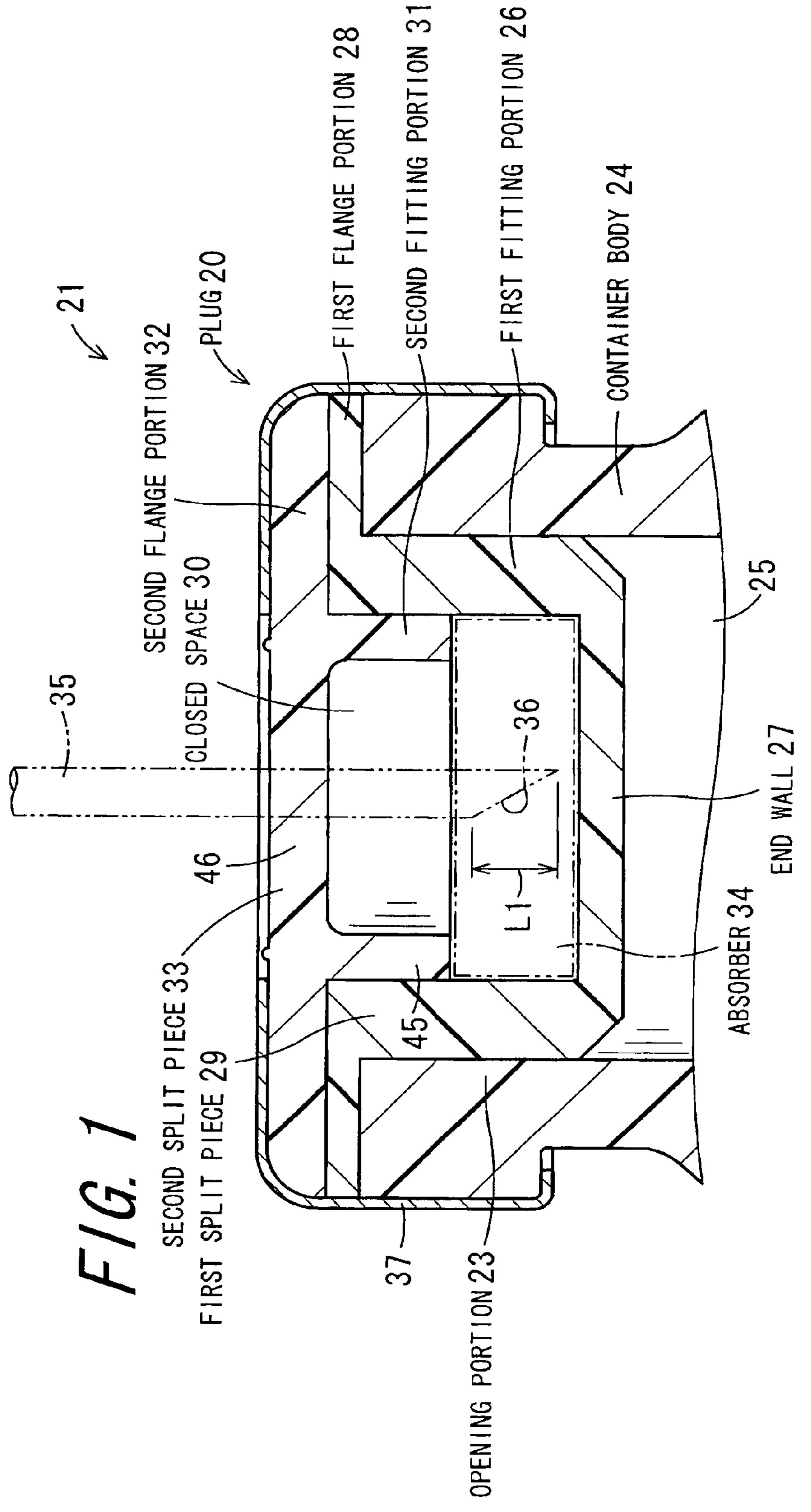
FIG. 1 is a partially enlarged cross-sectional view showing a vial sealed by a plug 20 for a container according to an embodiment of the invention.

FIG. 1 is a partially enlarged cross-sectional view showing a vial 21 sealed by a plug 20 for a container according to an embodiment of the invention. In the embodiment, the plug 20 used for the vial 21 as a container includes a first split piece 29 which has a cylindrical first fitting portion 26 that is mounted on an opening portion 23 of a bottomed cylinder-like container body 24 containing liquid 22 and fitted to an opening portion space 25 surrounded by the opening portion 23, an end wall 27 that blocks one end facing the opening portion space 25 of the first fitting portion 26, and a first flange portion 28 extending outwardly in a radial direction of the first fitting portion 26 from the other end thereof; a second split piece 33 which has a second fitting portion 31 with an inverted-U-shaped cross-section that forms a closed space 30 between the end wall 27 and the second fitting portion 31 by being fitted to the first fitting portion 26 of the first split piece 29, and a second flange portion 32 that extends outwardly in a radial direction of the second fitting portion 31 therefrom; a flat right cylindrical absorber 34 which is contained in the closed space 30 and formed of a liquid-absorbing material; and a protector cap 37 which mounts the first and second split pieces 29 and 33 mounted on the opening portion 23 on the opening portion 23 by caulking.

The first and second split pieces 29 and 33 are formed of a flexible and resilient material. The flexible and resilient material is mainly a thermosetting elastomer formed of synthetic rubber such as butyl rubber, silicone rubber, isoprene rubber, and butadiene rubber, and natural rubber, and realized by so-called vulcanized rubber material. The material may be a thermoplastic elastomer and a styrene-based elastomer such as an olefin-based resin including polypropylene, polystyrene, and the like.

The hardness of the first split piece 29 is selected from 1 to 90, and preferably from 10 to 80 (JIS-K6301). In addition, the hardness of at least a needle-inserting portion of the second split piece 33 is selected from 1 to 90, and preferably 10 to 80 (JIS-K6301). The hardness of the first and second split pieces 29 and 33 in this range is preferable in the respect that an injection needle 35 is easily inserted, formability becomes excellent in production, the injection needle 35 is inserted with high adhesiveness, and desired air-tightness and liquid-tightness are obtained.

In the closed space 30, provided that an axial direction length of a portion where an end surface 36 of a wedge-like tip portion of the injection needle 35 that is inserted through a partition wall 46 is L1, the end wall 27 of the first split piece 29 and the partition wall 46 of the second split piece 33 are separated from each other at an interval equal to or larger than the axial direction length L1.

The second fitting portion 31 includes a cylindrical fitting cylinder portion 45 and the partition wall 46 that extends inwardly in a radial direction of the fitting cylinder portion 45 from one end in an axial direction thereof. The partition wall 46 is formed to be approximately parallel with the end wall 27 of the first split piece 29, in a state in which the second split piece 33 is fitted to the first split piece 29, and the absorber 34 is contained in the closed space 30 between the partition wall 46 and the end wall 27. The absorber 34 is formed of a foamed synthetic resin having interconnected cells, for example. As the foamed synthetic resin having interconnected cells, sponge formed of a synthetic resin with chemical resistance may be used.

The liquid is a drug such as an anti-cancer drug having cytotoxicity, for example. This type of drug is prepared in an infusion solution, and when administered to a patient, and discarded, a healthcare professional who handles the vial 21 is at a risk of being exposed to the anti-cancer drug. Therefore, the opening portion 23 of the container body 24 is sealed by the plug 20 of the embodiment. The use of this type of plug 20 makes it possible to accomplish high air-tightness and liquid-tightness in any state of before and during the insertion of the injection needle 35 and during and after the removal of the injection needle 35.

Figure 2:
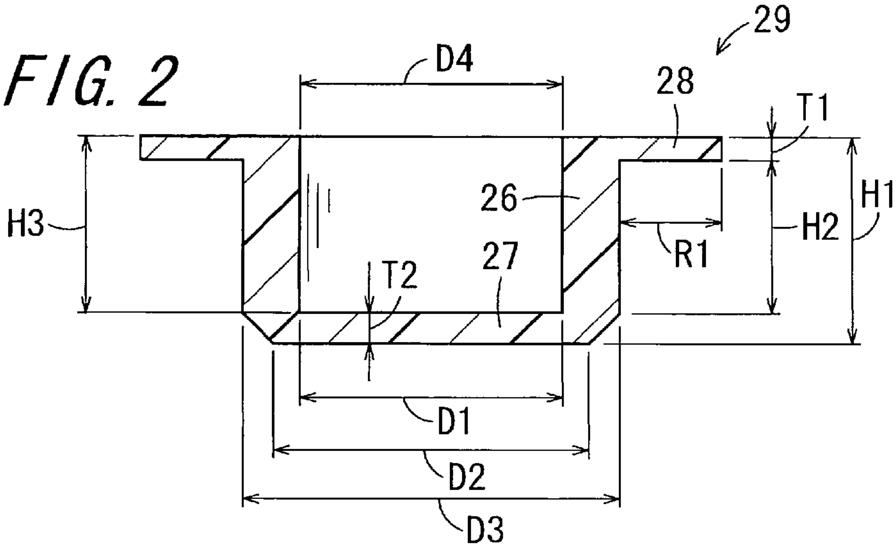
FIG. 2 is an enlarged cross-sectional view of a first split piece 29.

FIG. 2 is an enlarged cross-sectional view of the first split piece 29. The first split piece 29 is formed of a molded material made of thermosetting synthetic resin. An example of the respective dimensions of first split piece 29 is diameter D1=8 mm, D2=11 mm, D3=12.8 mm, D4=7 mm, height H1=8.3 mm, H2=5.5 mm, H3=6.5 mm, thickness T1=1.3 mm, T2=1.8 mm, and radius R1=3.2 mm.

Figure 3:
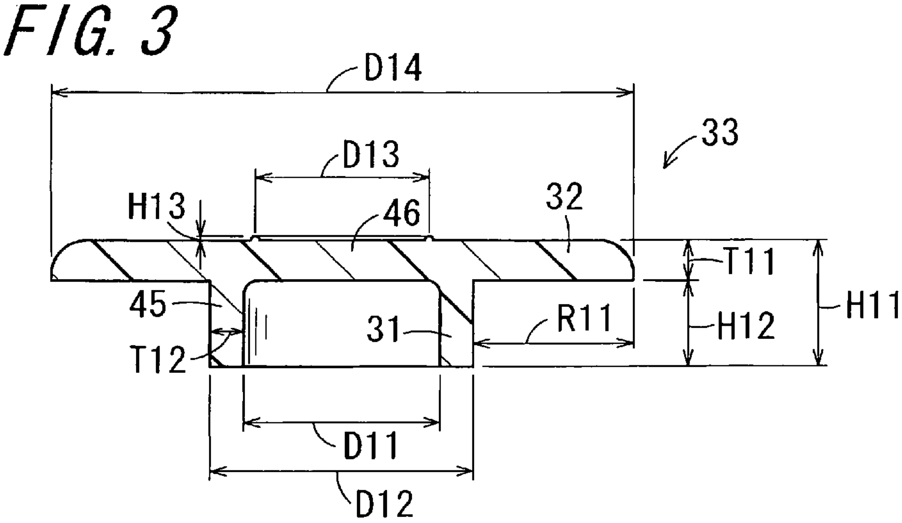
FIG. 3 is an enlarged cross-sectional view of a second split piece 33.

FIG. 3 is an enlarged cross-sectional view of the second split piece 33. The second split piece 33 is formed of a molded material made of a thermosetting synthetic resin. An example of the respective dimensions of the second split piece 33 is diameter D11=5 mm, D12=7.2 mm, D13=5 mm, D14=19.2 mm, height H11=6.5 mm, H12=4.5 mm, H13=0.2 mm, thickness T11=2 mm, T12=1.1 mm, and radius R11=6 mm.

Figure 4:
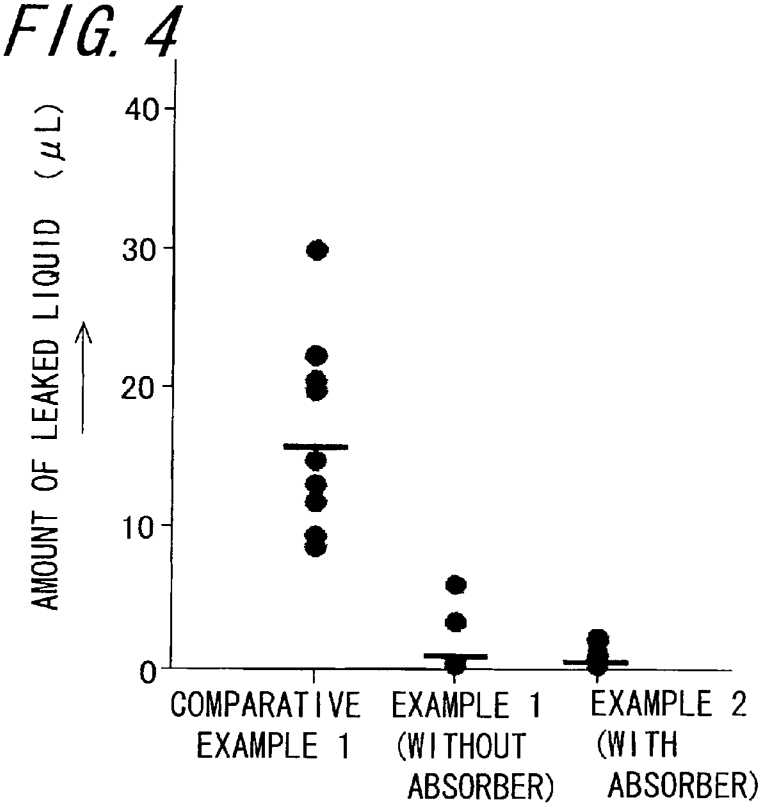
FIG. 4 is a graph showing measurement results of a leaked amount measured by the inventors.

FIG. 4 is a graph showing measurement results of a leaked amount measured by the inventors. In order to confirm the sealing performance of the plug according to the invention, the inventors carried out the following test on Comparative example 1 and Examples 1 and 2.

[Test Condition]

Type of drug solution: 100 mM sodium cinnamate aqueous solution

Property of drug solution: liquid

Environmental temperature: room temperature to 20° C.

Instrument for measuring amount of leaked drug solution: CAPI-3100 type capillary electrophoresis system (manufactured by OTSUKA ELECTRONICS CO., LTD.)

A measurement method of the amount of the leaked drug solution is as follows.

1) Leakage of Drug Solution

To the container body 24, 1 mL of the drug solution was introduced, and the plug 20 was assembled as shown in FIG. 1 and mounted on the opening portion 23 of the container body 24. The injection needle 35 was inserted into the plug 20 by 18G×1·½. Filter paper that had been cut into the same size as the internal diameter of the opening portion 23 of the container body 24 and had a slash cut from the circumference to the center was placed on the plug 20 so that the center of the filter paper was overlapped on the insertion portion. The container body 24, the filter paper, and the injection needle 35 were stood upside down, and the injection needle 35 was pulled while the container body 24 and the filter paper were kept so as not to be separated from each other. At this time, liquid attached to the filter paper was recognized as a leaked drug solution. This operation was repeated 9 times while replacing the container body 24, the filter paper, and the injection needle 35 with new ones for each operation.

2) Measurement of Amount of Leaked Drug Solution

Cinnamic acid included in the drug solution soaked into the filter paper was eluted in a constant volume of purified water. The elute was analyzed with UV-detection capillary electrophoresis, and the amount of the cinnamic acid included in the leaked liquid was measured by absolute quantitation, thereby calculating the volume of the leaked liquid. The measurement conditions were capillary: fused silica (an internal diameter of 50 μm, a length of 62 cm), migration liquid: 50 mM boric acid buffer (pH 10.5), voltage: 30 kV, detection wavelength: 270 nm, and measurement temperature: 25° C.

3) Specifications of Plug

Plug shape: see FIGS. 2 and 3

Material of plug: butyl rubber

Hardness of first split piece 29: hardness of 45
Hardness of second split piece 33: hardness of 45
Absorber shape: □7 mm×3 mm
Material of absorber: urethane sponge To calculate the average of the leaked amount, the total leaked amount in 9 operations was calculated and then divided by 9. To calculate the standard deviation thereof, the average of the leaked amount was subtracted from the leaked amount of each operation, and the resultant was squared, thereby calculating the sum of squared deviation. By dividing the sum of squared deviation by 9, variance was calculated, and the standard deviation was calculated by extracting the square root of the variance.

COMPARATIVE EXAMPLE 1

Material: butyl rubber, hardness of 45

Figure 10A:
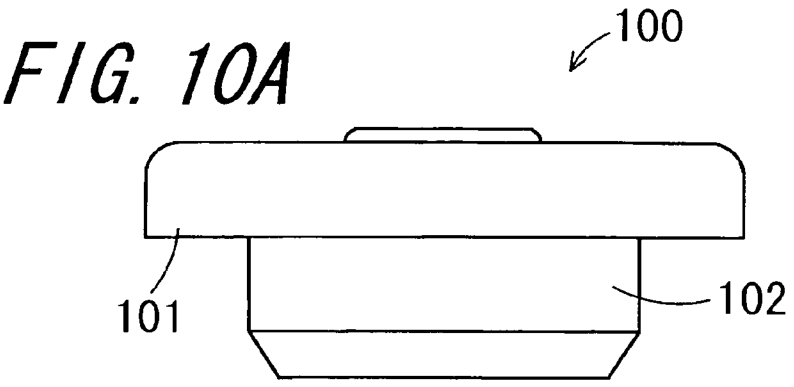
FIG. 10A is a front view of a plug 100 used as a comparative example.
Figure 10B:
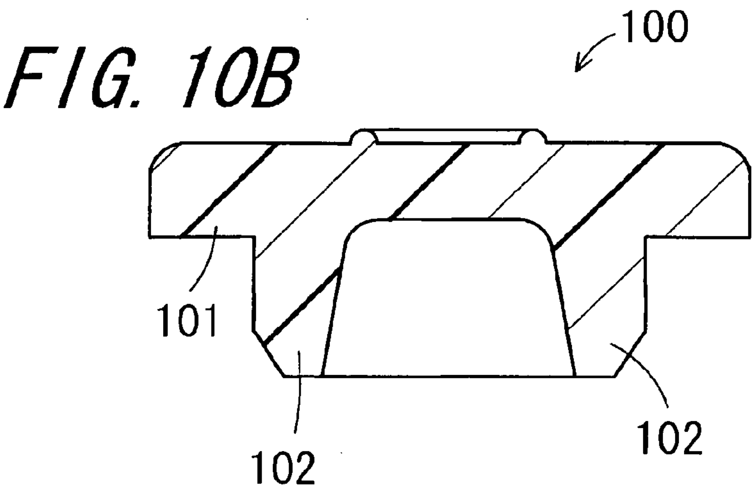
FIG. 10B is a cross-sectional view of the plug 100.

Shape: FIG. 10A is a front view of a plug 100 used as a comparative example, and FIG. 10B is a cross-sectional view of the plug 100. As shown in FIGS. 10A and 10B, the plug 100 is configured by a flange portion 101 that is placed on a flange 5 at the body side formed in an opening portion 3 of a container body 2, and a cylindrical peripheral wall 102 that includes one end connected to the inner peripheral portion of a flange portion 101 at a right angle and extends toward the container body.

EXAMPLE 1

Material: butyl rubber, hardness of 45
Shape: shown in FIGS. 2 and 3

EXAMPLE 2

Material: butyl rubber, hardness of 45

Shape: shown in FIGS. 2 and 3 (here, the absorber 34 is included in the closed space 30)

[Experimental Results]

The measurement results of the amount of leaked liquid measured using Comparative example 1 and the respective Examples 1 and 2 were as in the following Table 1.

TABLE 1

| | Comparative example 1 | Example 1 | Example 2 |
|---|---|---|---|
| Amount of leaked liquid (μl) | 19.8 | 0.0 | 2.0 |
| | 30.0 | 0.0 | 0.0 |
| | 14.8 | 0.0 | 1.8 |
| | 8.5 | 0.0 | 0.5 |
| | 11.8 | 3.1 | 0.2 |
| | 22.3 | 5.8 | 0.0 |
| | 9.3 | 0.0 | 0.0 |
| | 13.1 | 0.0 | 0.0 |
| | 20.5 | 0.0 | 0.8 |
| Average | 16.7 | 1.0 | 0.6 |
| Standard deviation | 7.0 | 2.1 | 0.8 |

Comparing the leaked amount of Comparative example 1 to the respective leaked amount of Examples 1 and 2, while the average of the amount of the leaked liquid was 16.7 μl in Comparative example 1, the amount of the leaked liquid was 1.0 μl and 0.6 μl respectively in Examples 1 and 2, which were markedly small amounts. Accordingly, it was confirmed that the amount of the leaked drug solution was more effectively suppressed compared to the related art.

According to the embodiment, the second fitting portion 31 of the second split piece 33 is fitted to the first fitting portion 26 of the first split piece 29, and the closed space 30 is formed between the end wall 27 of the first split piece 29 and the partition wall 46 of the second split piece 33. Therefore, by separating the first and second split pieces 29 and 33, it is possible to open the closed space 30, sterilize the inside of the closed space 30, and to remove foreign substances in the closed space 30.

This type of plug 20 may be mounted on the opening portion 23 of the container body 24 in a state in which the first fitting portion 26 of the first split piece 29 is fitted to the second fitting portion 31 of the second split piece 33 so as to combine the first split piece 29 with the second split piece 33. Alternatively, after the first split piece 29 is mounted on the opening portion 23 of the container body 24, the second fitting portion 31 of the second split piece 33 may be fitted to the first fitting portion 26 of the first split piece 29.

In a state in which the first split piece 29 and the second split piece 33 are combined with each other in this manner and mounted on the opening portion 23 of the container body 24, the outer peripheral surface of the first fitting portion 26 comes into contact with the inner peripheral surface of the opening portion 23 of the container body 24, and the first flange portion 28 comes into contact with the end surface of the opening portion 23 of the container body 24. Since the second fitting portion 31 is fitted to the first fitting portion 26, the first fitting portion 26 is pressed outwardly in the radial direction thereof by the second fitting portion 31. Due to this pressing force, the outer peripheral surface of the first fitting portion 26 tightly adheres to the inner peripheral surface of the opening portion 23 of the container body 24, whereby the high air-tightness and liquid-tightness can be accomplished. In addition, since the second split piece 33 includes the second flange portion 32, the first flange portion 28 is pressed on the opening portion 23 of the container body 24 by the second flange portion 32, so the first flange portion 28 tightly adheres to the end surface of the opening portion 23 of the container body 24. This also makes it possible to accomplish the high air-tightness and liquid-tightness.

Since the first and second flange portions 28 and 32 are provided while being placed on the opening portion 23 of the container body 24, the end wall 27 formed while being connected to an in-plate direction of the first flange portion 28 and the partition wall 46 formed while being connected to an in-plate direction of the second flange portion 32 are tightly held on the opening portion 23 by the protector cap 37. Therefore, the end wall 27 and the partition wall 46 more easily undergo elastic deformation compared to the first and second flange portions 28 and 32, and when the inserted injection needle 35 is taken out from the end wall 27 and the partition wall 46, the end wall 27 and the partition wall 46 undergo elastic deformation outwardly (toward an upper side in FIG. 1) due to the sliding friction force between the injection needle 35 and the end wall 27 and the sliding friction force between the inserted injection needle 35 and the partition wall 46.

Consequently, when the injection needle 35 is taken out from the end wall 27, even if the liquid in the container body 24 leaks inside the closed space 30 from the gap between the crack of the end wall 27, which is formed due to the insertion of the injection needle 35, and the injection needle 35, the partition wall 46 undergoes elastic deformation outwardly due to the sliding friction force caused by pulling of the injection needle 35. Accordingly, a negative pressure is created in the closed space 30, and the negative pressure is introduced to the gap between the crack of the partition wall 46 and the injection needle 35.

As a result, when the injection needle 35 is taken out from the partition wall 46, it is possible to reliably prevent the liquid from leaking outside from the gap between the crack of the partition wall 46 and the injection needle 35. Moreover, since the first and second split pieces 29 and 33 can be easily realized by a well-known method such as compression molding that uses a metal mold, it is possible to produce the leakage-free plug 20 at a low cost.

In addition, according to the embodiment, the absorber 34 formed of a liquid-absorbing material is contained in the closed space 30. Therefore, when the injection needle 35 is inserted into the container body 24 through the partition wall 46 and the end wall 27, and when the injection needle 35 that has been inserted into the container body 24 is pulled, even if the drug solution in the container body 24 leaks inside the closed space 30 through the gap between the inner surface of the crack that is formed due to the insertion of the injection needle 35 into the end wall 27 and the injection needle 35, the leaked liquid is absorbed into the absorber 34. Consequently, it is possible to more reliably prevent the liquid from leaking outside through the gap between the inner surface of the crack that is formed due to the insertion of the injection needle 35 into the partition wall 46 and the injection needle 35.

Furthermore, according to the embodiment, the closed space 30 is configured to have an interval equal to or larger than the axial direction length L1 of the end surface 36 of the tip portion of the injection needle 35. Consequently, a period is not created in which the tip portion of the injection needle 35 is partially present in both the end wall 27 and the partition wall portion 46 at the same time. Accordingly, while the injection needle 35 is taken out from the end wall 27 and the partition wall 46, when the wedge-like tip portion of the injection needle 35 passes through the end wall 27, a right cylindrical portion that is closer to the base portion than to the tip portion of the injection needle 35 passes through the partition wall 46, and the partition wall portion 46 uniformly contacts almost the entire outer peripheral surface of the injection needle 35. Accordingly, a state is prevented in which the crack formed in the end wall 27 and the crack formed in the partition wall 46 are not incompletely closed at the same time, and it is possible to more reliably prevent the leakage of liquid.

Furthermore, according to the embodiment, the leakage of liquid can be suppressed with a high sealing performance by the plug 20 described above. Therefore, when the liquid is a drug solution such as an anti-cancer drug with high volatility, the handler of the vial 21 is prevented from being exposed to the drug solution, and it is possible to further improve the safety with respect to the exposure to the drug solution at a low cost.

Figure 5:
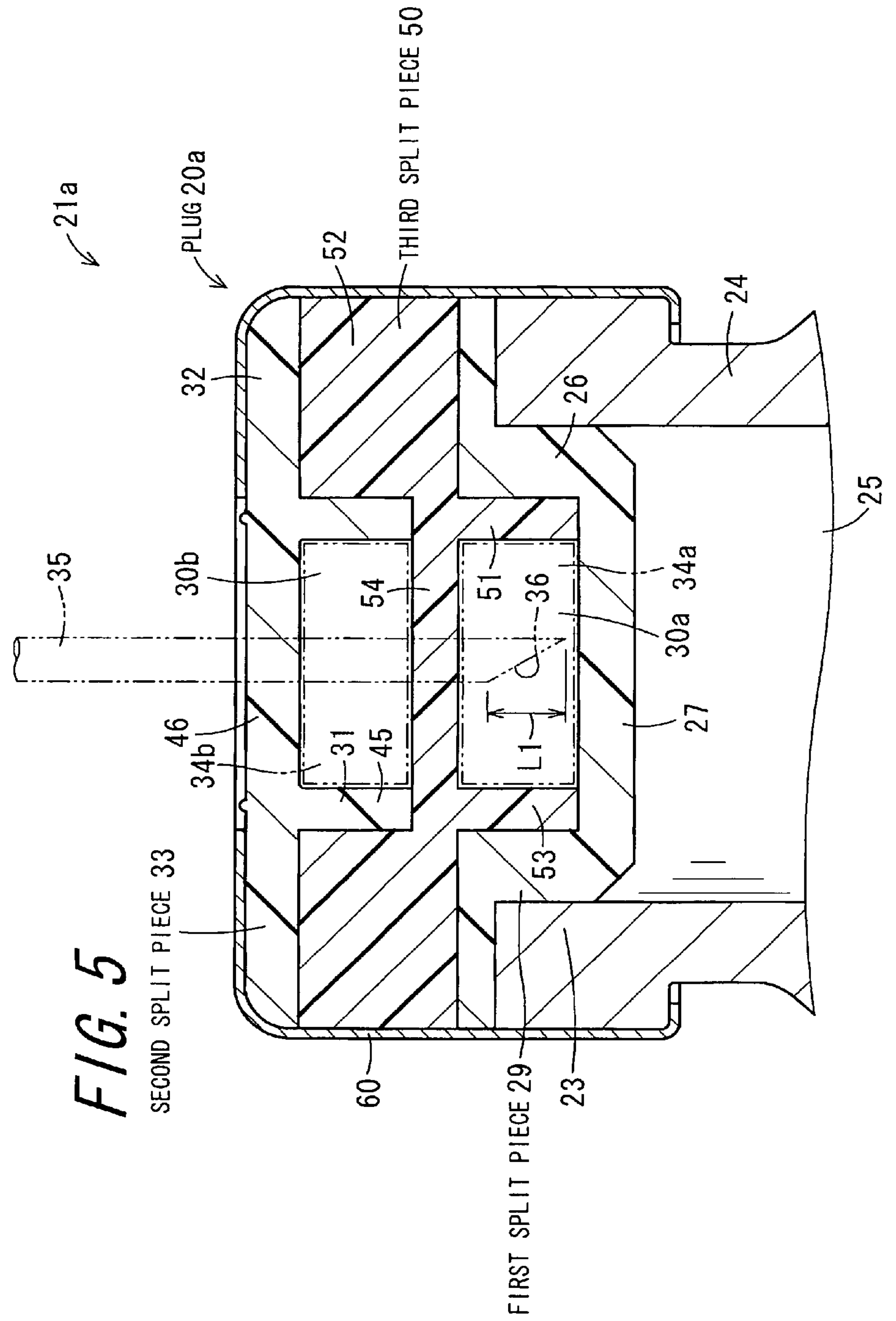
FIG. 5 is a partial cross-sectional view showing a vial 21*a* sealed by a plug for a container according to another embodiment of the invention.

FIG. 5 is a partial cross-sectional view showing a vial 21*a* sealed by a plug 20*a* for a container according to another embodiment of the invention. The portions corresponding to those of the embodiment described above are denoted by the same reference numerals. The plug 20*a* for a container of the present embodiment has a configuration in which a third split piece 50 is interposed as an intermediate split piece between the first split piece 29 and the second split piece 33, the third split piece 50 is sandwiched between the first split piece 29 and the second split piece 33 on the same axis, and the first to third split pieces 29, 33, and 50 are fastened to the opening portion 23 of the container body 24 by a protector cap 60.

The third split piece 50 includes a third fitting portion 51 with an inverted-U-shaped cross-section that is fitted to the first fitting portion 26 of the first split piece 29 and forms a first closed space 30*a* between the end wall 27 and the third fitting portion 51, and a cylindrical peripheral wall 52 that extends outwardly in a radial direction of the third fitting portion 51 therefrom and protrudes to one side in an axial direction thereof from the third fitting portion 51. The third fitting portion 51 includes a cylindrical fitting cylinder portion 53 and a partition wall 54 formed extending inwardly in a radial direction of the fitting cylinder portion 53 from one end in an axial direction thereof.

The first closed space 30*a* is formed between the end wall 27 of the first split piece 29 and the partition wall 54 of the third split piece 50, and a second closed space 30*b* is formed between the partition wall 54 of the third split piece 50 and the partition wall 46 of the second split piece 33. The respective closed spaces 30*a* and 30*b* have an interval equal to or larger than the axial direction length L1 of the end surface 36 of the tip portion of the inserted injection needle 35, and contain absorbers 34*a* and 34*b* respectively that are the same as the absorber 34 of the embodiment described above.

According to the configuration of the embodiment, the first and second closed spaces 30*a* and 30*b* are formed, and the absorbers 34*a* and 34*b* are contained in the closed spaces 30*a* and 30*b*, respectively. Accordingly, it is possible to more reliably prevent the leakage of the drug solution caused when injection needle is taken out from the end wall 27 and the respective partition wall portions 46 and 54.

Figure 6:
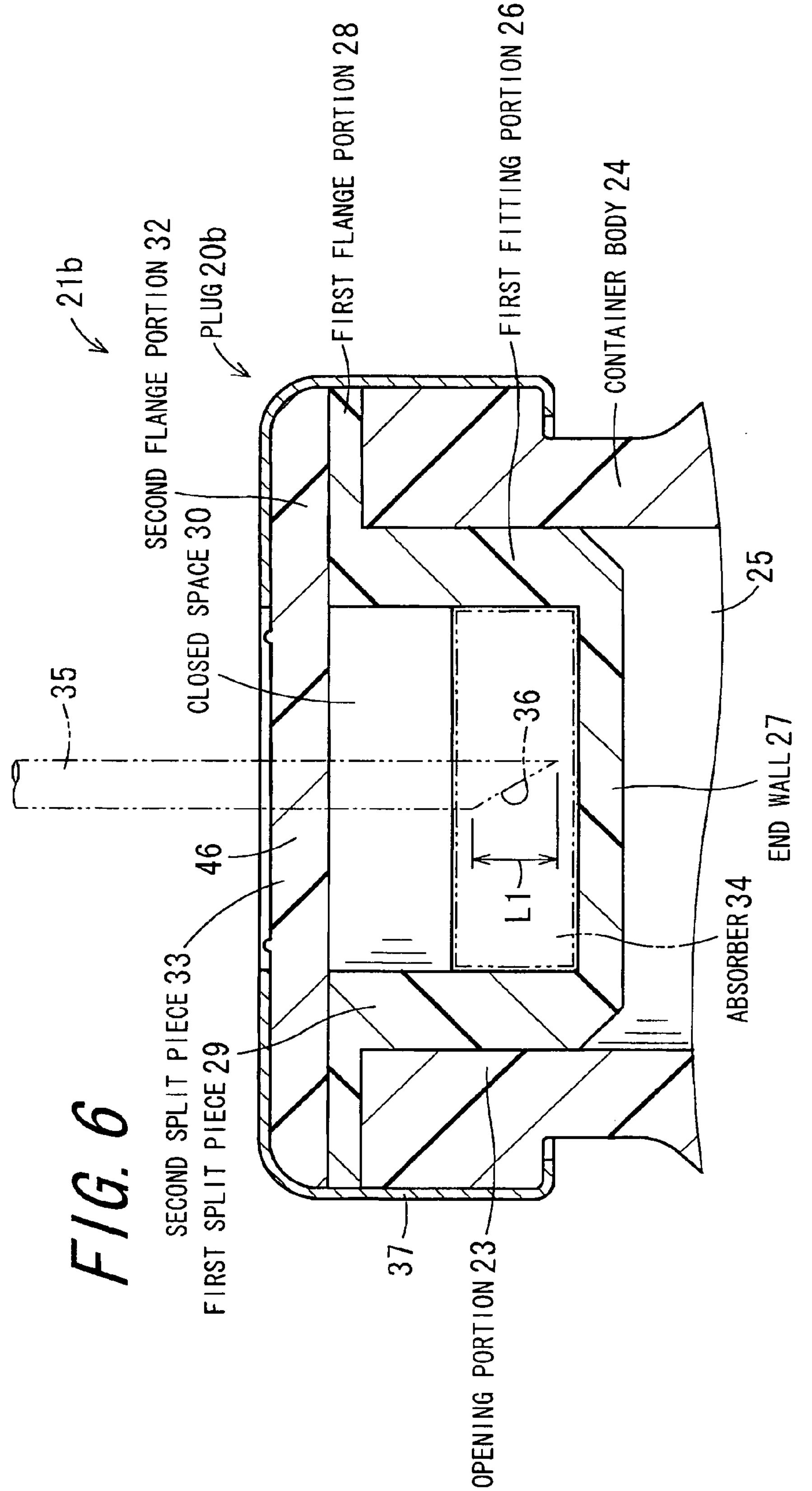
FIG. 6 is a partially enlarged cross-sectional view showing a vial 21*b* sealed by a plug 20*b* of a container according to still another embodiment of the invention.

FIG. 6 is a partially enlarged cross-sectional view showing a vial 21*b* sealed by a plug 20*b* of a container according to still another embodiment of the invention. Portions corresponding to those of the embodiment described above are denoted by the same reference numerals, and the repeated description thereof is omitted. Though similar to the plug 20 of the embodiment in FIG. 1, the plug 20*b* of the present embodiment is different from the plug 20 in that the second fitting portion 31 described above is not provided in the second split piece 33.

This type of plug 20*b* is formed of a circular plate-like molded body in which the partition wall 46 is integrally formed while being connected to an in-plane direction of the second flange portion 32. Similarly to the embodiment described above, the first flange portion 28 and the second flange portion 32 are tightly held on the opening portion 23 by the protector cap 37, in a state in which the second flange portion 32 is placed on the first flange portion 28.

According to the plug 20*b* configured in this manner, the partition wall 46 is caused to flexibly undergo elastic deformation by the sliding friction force caused by the pulling of the injection needle 35, a negative pressure is created in the closed space 30 accordingly, and the negative pressure is introduced to the gap between the crack of the partition wall 46 and the injection needle 35, whereby it is possible to reliably prevent the liquid from leaking inside the closed space 30.

Figure 7:
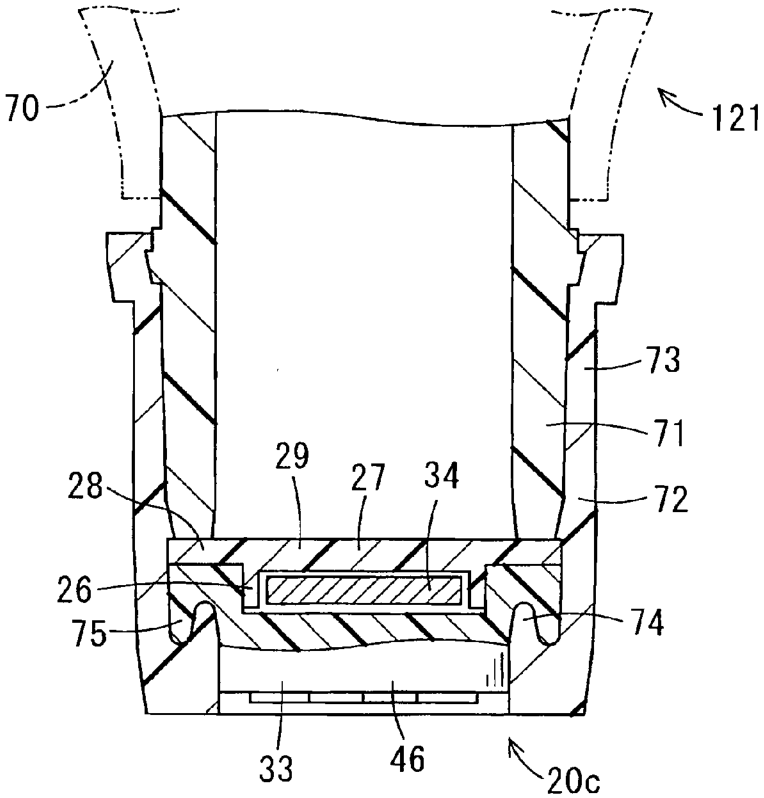
FIG. 7 is a partially enlarged cross-sectional view showing an infusion bag 121 sealed by a plug 20*c* of a container according to still another embodiment of the invention.
Figure 8:
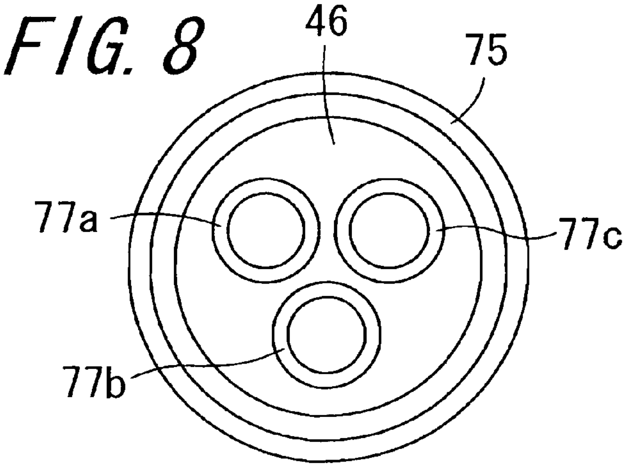
FIG. 8 is a front view of the plug 20*c* taken when

FIG. 7 is a partially enlarged cross-sectional view showing an infusion bag 121 sealed by a plug 20*c* of a container according to still another embodiment of the invention. FIG. 8 is a front view of the plug 20*c* taken when FIG. 7 is seen from below. Portions corresponding to those of the embodiment described above are denoted by the same reference numerals, and the repeated description thereof is omitted. The plug 20*c* of the present embodiment is mounted on an opening portion 71 of a pouch-like bag 70 made of polypropylene as a container body by a cap 72. The cap 72 includes a cylindrical portion 73 with an approximately right cylindrical shape, and an engagement claw portion 74 that is connected to the inner peripheral portion of one end of the cylindrical portion 73 and protrudes toward the other end of the cylindrical portion 73.

The plug 20*c* includes the first split piece 29 in which the end wall 27 is formed in one end of the first fitting portion 26, and the first flange portion 28 is integrally formed extending outwardly in the radial direction of the end wall 27 therefrom; and the second split piece 33 in which an engagement projection portion 75, which is engaged between the engagement claw portion 74 and one end portion of the cylindrical portion 73 by being fixed therebetween, is formed in the outer peripheral portion thereof. In the partition wall 46 of the second split piece 33, circular ring-like protuberant portions 77*a*, 77*b*, and 77*c* that indicate an insertion position of the injection needle 35 are axisymmetrically formed. The closed space 30 is formed between the end wall 27 of the first split piece 29 and the partition wall portion 46 of the second split piece 33, and the absorber 34 is contained in the closed space 30. The first flange portion 28 and the engagement projection portion 75 are tightly held between the end surface of the opening portion 71 and the engagement claw portion 74 of the cap 72, whereby the air-tightness and the liquid-tightness are accomplished.

In this type of infusion bag 121, it is also possible to reliably prevent the liquid from leaking when the injection needle 35 that has been inserted in the respective protuberant portions 77*a*, 77*b*, and 77*c* of the partition wall 46 is taken out, similarly to the embodiment described above.

In still another embodiment of the invention, a configuration may be employed in which the closed spaces 30; 30*a* and 30*b* are not provided with the absorbers 34; 34*a* and 34*b*. Alternatively, a water-absorptive polymer may be contained in the closed space instead of the absorbers 34; 34*a* and 34*b*, and the water-absorptive polymer may be contained in the closed space together with the absorbers 34; 34*a* and 34*b*. Examples of the water-absorptive polymer include sodium polyacrylate.

In this manner, if the absorbers 34; 34*a* and 34*b* are contained in the closed spaces 30; 30*a* and 30*b*, or if only the water-absorptive polymer is contained, or if both the absorbers 34; 34*a* and 34*b* and the water-absorptive polymer are contained, it is possible to capture the liquid that permeates the closed spaces 30; 30*a* and 30*b*, and to more reliably prevent the liquid from leaking outside from the crack of the partition wall.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

20, 20*a*: Plug
21, 21*a*, 21*b*: Vial
22: Liquid
23: Opening portion
24: Container body
25: Opening portion space
26: First fitting portion
27: End wall
28: First flange portion
29: First split piece
30; 30*a*, 30*b*: Closed space
31: Second fitting portion
32: Second flange portion
33: Second split piece
34: Absorber
35: Injection needle
36: End surface
37: Protector cap
45: Fitting cylinder portion
46, 54: Partition wall
50: Third split piece

The invention claimed is:

1. A plug for a container comprising:

a first split piece formed of a flexible and resilient material, the first split piece having a cylindrically-shaped first fitting portion with an open cavity defined by vertical sidewalls and an end wall that is positioned horizontally in relation to the vertical sidewalls, the first fitting portion being configured to fit into an opening of a container body containing liquid, the end wall being on a distal-most end of the sidewalls and configured to block the opening of the container body, the first split piece including a first flange portion extending outwardly in a radial direction from a proximal-most end of the sidewalls of the first fitting portion; and a second split piece formed of a flexible and resilient material, the second split piece having a partition wall with a bottom surface configured to seal the open cavity of the first fitting portion, the partition wall having a second flange portion extending outwardly in a radial direction from the partition wall, the partition wall and the second flange portion combining to form a substantially flat top surface of the second split piece which opposes the bottom surface of the partition wall, a circumference of the first flange portion being substantially equal to a circumference of the second flange portion, wherein the first fitting portion includes an outer peripheral surface which is configured to contact an inner peripheral surface of the opening.

2. The plug for a container of claim 1, wherein an absorber formed of a liquid-absorbing material is contained in the sealed cavity.

3. The plug for a container of claim 1, wherein the liquid is a drug solution.

4. The plug for a container of claim 1, wherein a water-absorptive polymer is contained in the sealed cavity.

5. The plug of claim 1, wherein the second split piece includes a second fitting portion extending away from the bottom surface of the partition wall and configured to be fitted into the first fitting portion such that the first fitting portion is pressed outwardly in the radial direction thereof by the second fitting portion.

6. The plug of claim 1, wherein, the first flange portion defines an upper surface of the first split piece, the second flange portion directly contacts and entirely covers the upper surface of the first split piece.

* * * * *

UNITED STATES PATENT AND TRADEMARK OFFICE

CERTIFICATE OF CORRECTION

PATENT NO. : 8,888,756 B2
APPLICATION NO. : 13/138803
DATED : November 18, 2014
INVENTOR(S) : Shunji Ishiwata et al.

It is certified that error appears in the above-identified patent and that said Letters Patent is hereby corrected as shown below:

ON THE TITLE PAGE

(73) Assignee should read: GTO Ltd., Osaka (JP)
KINKI UNIVERSITY, Osaka (JP)

Signed and Sealed this
Third Day of May, 2016

Michelle K. Lee
*Director of the United States Patent and Trademark Office*